United States Patent [19]

Fischell

[11] Patent Number: 4,941,461
[45] Date of Patent: Jul. 17, 1990

[54] ELECTRICALLY ACTUATED INFLATABLE PENILE ERECTION DEVICE

[76] Inventor: Robert E. Fischell, 14600 Viburnum Dr., Dayton, Md. 21036

[21] Appl. No.: 403,086

[22] Filed: Sep. 5, 1989

[51] Int. Cl.$^5$ .............................................. A61F 2/26
[52] U.S. Cl. .................................................... 128/79
[58] Field of Search .......................... 128/79, DIG. 25; 623/24, 26

[56] References Cited

U.S. PATENT DOCUMENTS 4,584,994 4/1986 Bamberger et al. ................... 128/79
4,711,231 12/1987 Finegold et al. ...................... 128/79

Primary Examiner—Cary E. Stone

[57] ABSTRACT

Disclosed is an electrically actuated penile erection prosthetic device. This device utilizes an alternating magnetic field generated from a device external to the patient which is inductively coupled into a pick-up coil that is implanted either within the corpus cavernosum of the penis or subcutaneously in the abdomen. The electrical energy from the pick-up coil is used to power an implanted pump that can pump saline solution from an implanted reservoir into the pendulous portion of the penile erection device. One embodiment of the reservoir is a collapsible root portion of the penile erection device or alternatively, the reservoir could be implanted within the abdomen.

28 Claims, 4 Drawing Sheets

ELECTRICALLY ACTUATED INFLATABLE PENILE ERECTION DEVICE

FIELD OF USE

This invention is in the field of penile prostheses for the treatment of erectile impotence.

BACKGROUND OF THE INVENTION

The use of inflatable penile prostheses is well known for the treatment of erectile impotence. One such device uses a pumping mechanism in the scrotum to inflate two fluid filled silicon rubber cylinders located in the corpora carvenosa of the penis from a fluid reservoir located in the abdomen. A disadvantage of this type of device is that it requires the patient to have considerable manual dexterity and also requires a rather large object to be placed in the scrotum.

U.S. Pat. No. 4,572,168 by R. E. Fischell describes a change-of-state pressurant in a reservoir placed in the abdomen that can force inflation fluid into the penile cylinders without the disadvantages of the scrotal pump. However, manual manipulation of an abdominal or penile valve by the user is still required to operate that Fischell invention.

BRIEF DESCRIPTION OF THE INVENTION

Ideally the entire prosthesis is located only in the penis (including its root) and requires no manual pumping by the patient in order to obtain the erect state. Thus the present invention uses two cylinders one each located in the two corpora carvenosa of the penis. A pulsatile, solenoid pump is located between the root and pendulous portions of each penile cylinder. The pump operates only when a coil of wire located in the wall of the elastomer cylinder is excited by an alternating magnetic field which originates from a torroidally shaped wire coil located in an "erection wand" that is actuated after being placed over the base of the pendulous portion of the penis. The erection wand is recharged from ordinary house current by well known techniques. The erect state is obtained by pumping the fluid from the root portion to the pendulous portion of the penile cylinder thus collapsing the elastomer walls of the root while expanding and stiffening the pendulous portion of the cylinder The pulsatile pump makes a humming vibratory sound when activated thus assuring the user that the erection wand is placed properly at the base of the penis. As soon as the erect state is achieved, the erection wand is removed and sexual intercourse can be accomplished. When the flaccid state is desired, the man squeezes his penis to a pressure of greater than 15 psig which causes a check valve located adjacent to the pulsatile pump to open thereby transferring the fluid back into the root chamber of the cylinder.

Thus it is an object of this invention to cause the erect state of the penis to be created by magnetically coupling energy into an implanted induction coil which in turn causes a solenoid actuated pulsatile pump to pump fluid from the root chamber to the pendulous portion chamber of a fluid filled, elastomer cylinder located in the corpus carvenosum of the penis.

Another object of this invention is to have the pump operate at a high speed (e.g. up to 1000 Hz) so as to effect the erect state in less than 30 secs.

Still another object of this invention is to accomplish the transfer of energy to operate the pump from a rechargeable erection wand with a torroidally shaped portion that passes over the base of the penis.

Still another object of the invention is to cause perceptible vibration of the pulsatile pump when it operates so as to indicate proper positioning of the erection wand.

Still another object of the invention is to design the valving system so as to disallow excess pressurization of the pendulous portion of the implanted elastomer cylinders.

Still another object of the invention is to cause the flaccid state to be obtained by manually squeezing the pendulous portion of the penis thus forcing the fluid through a check valve back into the root section of the penis.

DETAILED DESCRIPTION OF THE INVENTION

Figure 1:
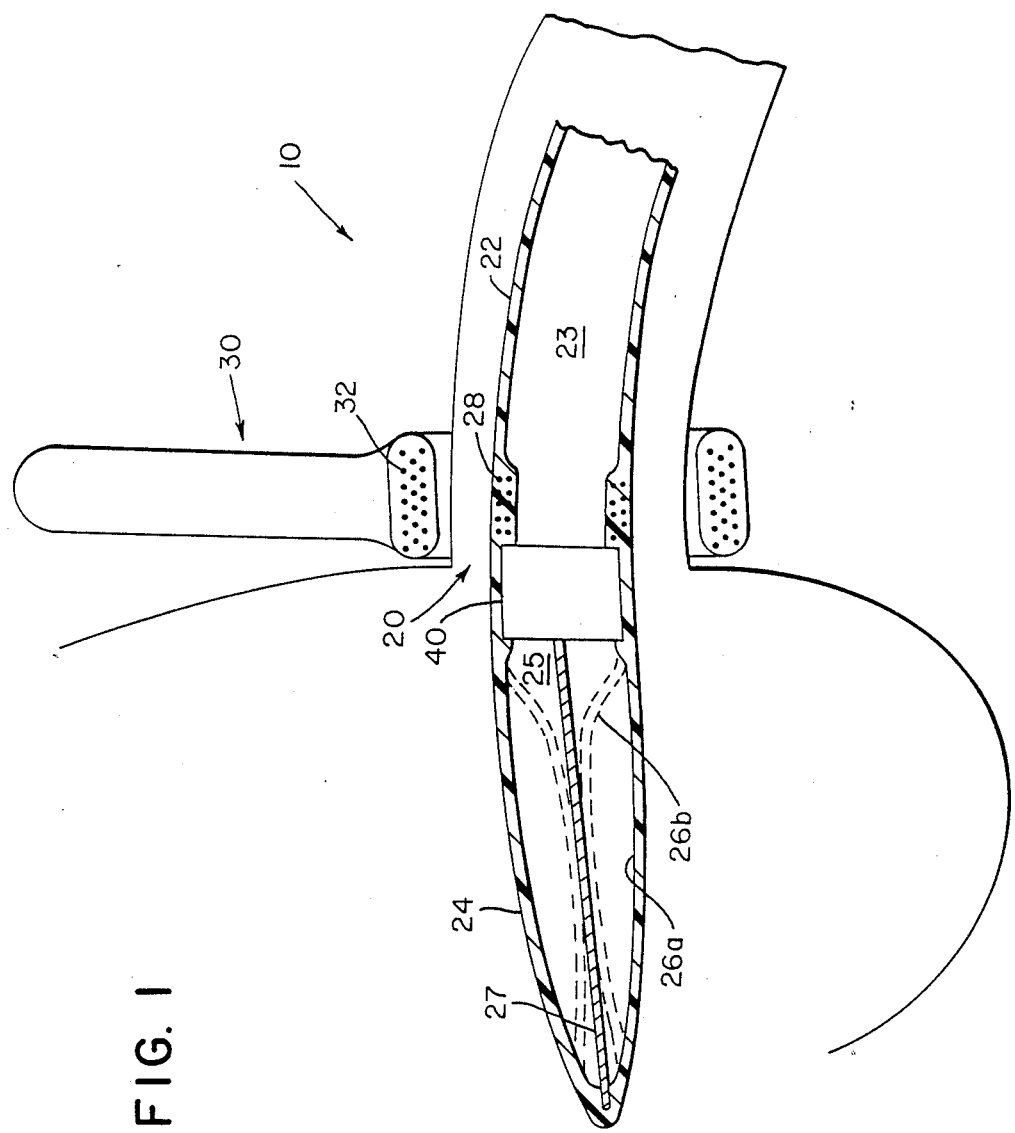
FIG. 1 is a cross-sectional view of penile cylinder which also shows the cross section of the erection wand.

FIG. 1 is a cross-sectional view of the electrically actuated penile erection apparatus 10, the cylinder 20 and the erection wand 30. The cylinder 20 has a pendulous portion 22 with a pendulous chamber 23 and a root portion 24 with a root chamber 25.

When the wand coil 32 is placed over the base of the penis and is turned on, a high intensity alternating electric current in the coil 32 causes an alternating magnetic field to be impressed over the penile cylinder coil 28 which is cast into the elastomer wall of the pendulous portion 22. By means of the electric circuit (shown in FIG. 3) that is physically located in the pump unit 40, the alternating current that is produced in the coil 28 is rectified and is used to charge a capacitor which is cyclically discharged into the solenoid pump which causes the fluid to be pumped from the root chamber 25 to the pendulous chamber 23. When the cylinder 20 is in the flaccid state, the root portion 24 has its elastomer wall in position 26a. When the fluid is pumped from the root chamber 25 to the pendulous chamber 23, the elastomer wall moves to the position 26b as shown by the dotted lines in FIG. 1.

Although in FIG. 1 the pumping unit 40 is shown between the root chamber 25 and the pendulous chamber 23, the pumping unit could be situated elsewhere in the cylinder 20 as long as the fluid was able to be pumped by tubing from the root chamber 25 to the pendulous chamber 23.

A rigid, preferably metal, member 27 could be used to keep the root portion 24 as a rigid foundation support for the cylinder 20 when the erect state is achieved.

Figure 2:
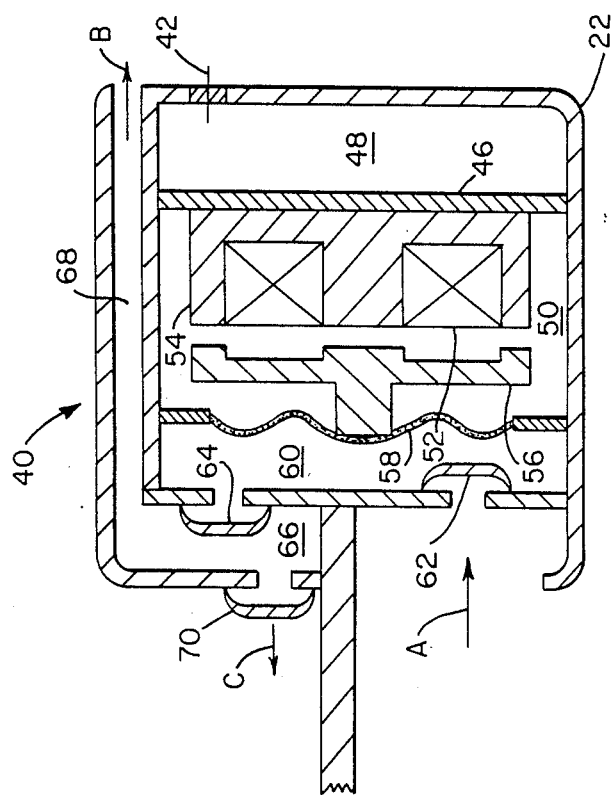
FIG. 2 is a schematic diagram of the pump unit showing the check valve and the electronics chamber.

FIG. 2 is a cross-sectional view of the pump unit 40 which (as seen in FIG. 1) separates the root chamber 25 from the pendulous chamber 23. The coil 28 (of FIG. 1) is attached to two hermetically sealed, feed-thrus 42 (only one is shown) which penetrate the hermetically sealed enclosure 44 of the pump unit 40. An internal wall 46 separates the electronics chamber 48 from the solenoid chamber 50. The environment of the solenoid chamber 50 would typically be a vacuum. The environment of the electronics chamber 48 would typically be a vacuum or dry nitrogen.

Figure 3:
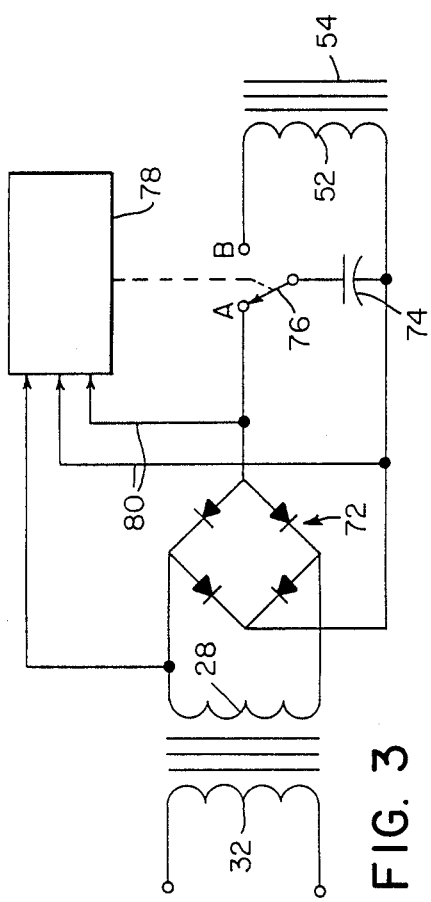
FIG. 3 is a schematic circuit diagram of the electronics section of the pump unit.

The electromagnet coil 52 is cyclically energized with electric current from the discharge of a capacitor (as shown in FIG. 3) which causes the magnetic armature 56 to be cyclically attracted to the electromagnet core 54 which in turn causes the diaphragm 58 to cyclically move back and forth in the pumping chamber 60. The pumping chamber 60 is filled with the same normal saline solution that fills the root chamber 25 and the pendulous chamber 23. When the armature 56 moves to the right (in FIG. 2), i.e., when the coil 52 is actuated, the diaphragm 58 moves to the right, causing the intake valve 62 to open and causing fluid to move into the pump chamber 60 from the root chamber 25. As soon as the armature 56 is in contact with the electromagnet core 54, the intake valve begins to close by means of spring actuation (not shown) and the spring force of the diaphragm 58 causes it to move to the left which in turn opens the outlet vavle 64 valve 64 which results in fluid entering the output chamber 66. The saline inflation fluid then passes through the passageway 68 into the pendulous chamber 23. By high rate (nominally 100 Hz) actuation of the coil 52, fluid is pumped from the root chamber 25 to the pendulous chamber 23 in fluid pulses at that same 100 Hz rate. For a nominal pump displacement of 0.003 milliliters per stroke, the pumping rate will be $100 \times 0.003 = 0.3$ ml/sec. Thus the typically required displacement of fluid from the root chamber 25 to the pendulous chamber 23 of 4.5 ml can be accomplished in 15 secs. This would be a reasonable time for the man to hold the erection wand 30 over the base of the penis in order to achieve the erect state. For larger pump displacements, e.g., 0.03 ml, the pumping rate could be reduced to 10 Hz. For smaller pump displacements, e.g., 0.0003 ml, the pumping rate might be increased to 1000 Hz. The erection wand is promptly removed from the penis after the erect state is achieved.

It is very important that a solenoid type pump be used for this application because at 100 Hz it provides a humming sound which is clearly perceived by the user as an indication that the pump is pumping, i.e., that the erection wand is properly placed at the base of the penis. Further, the amplitude of the solenoid pump vibration will change when the root chamber 25 is drained because the diaphragm 58 will not as easily move to the right (FIG. 2) and the valves 62 and 64 will therefore have a lesser displacement. This change of vibration amplitude will indicate to the user that the hardest erect state has been attained. He can then turn off and remove the erection wand.

When the flaccid state is desired, the patient firmly squeezes his penis which causes the check valve 70 to open which in turn causes fluid to flow from the pendulous chamber 23 through the passageway 68, into the output chamber 66 and finally back into the root chamber 25. Intake valve 62 and output valve 64 are typically spring loaded to open at a pressure of between 0.5 and 5.0 psid. The check valve 70 is typically designed to operate at a pressure of approximately 15 psid. Thus the pressure in pendulous chamber 23 is limited to not more than the approximately 15 psid setting of the check valve 70. This effectively prevents over pressurization of the elastomer walls of the pendulous portion 22. This is important since otherwise excessive running of the pump could permanently damage the elastomer walls of the pendulous portion.

If the valves 62 and 64 have their opening pressures set at 0.5 psid, then the root chamber 25 can only have a total of 1.0 psid greater pressure than the pendulous chamber 23. Preferably, the valves 62 and 64 will be set at 2.5 psid to achieve a 5.0 psi difference between the root chamber 25 and the pendulous chamber 23 which provides a better flaccid state condition.

In FIG. 2, the arrows A and B show the direction of fluid flow from the root chamber 25 to pendulous chamber 23 when the pumping unit 40 is actuated. The arrow C shows the direction of the fluid flow when the pendulous portion is firmly squeezed (at greater than 15 psid) thus achieving the flaccid state.

The materials of all parts of the pumping unit 40 except the magnetic coil 52, electromagnet core 54 and the elastomer portions of the poppets of the valves 62, 64 and 70 are typically made from pure titanium or the titanium alloy Ti-6Al-4V. The coil 52 would be standard copper magnet wire; the electromagnet core 54 would typically be made from thin laminations of a high permeability alloy such as 50% nickel and 50% iron; silicone rubber would typically be used for the elastomer portion of the valve poppets. It is presumed that the valves 62, 64 and 70 would use hard metal (titanium) seats and would have soft, elastomer molded inserts attached to a titanium frame of the valve poppet.

Figure 4:
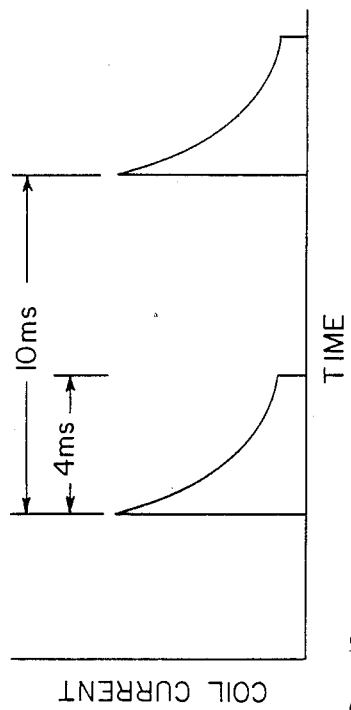
FIG. 4 is a graph of the current in the coil of the electromagnet of the pulsatile solenoid pump.

FIG. 3 is an electrical schematic showing the wand coil 32, the pick-up induction coil 28 and the electric circuit elements that are contained within the electronics chamber 48 of the pump unit 40 (FIG. 2). When a high frequency (approximately 50 kHz) alternating current is coupled from the wand coil 32 by magnetic induction into the coil 28, the full wave rectifier 72 creates a fluctuating d-c voltage that is used to charge the capacitor 74 when the switch 76 is in position A. When the switching circuit 78 causes the switch 76 to move to the position B, the capacitor 74 discharges across the coil 52 which results in a coil current as shown in FIG. 4. The coil current causes the electromagnet core 54 to be magnetized thus actuating the pumping action as previously described. As seen in FIG. 4, for a 100 Hz frequency, the capacitor would typically be charged for 6 ms and discharged for 4 ms. The switching circuit 78 would have its d-c power provided by lines 80 and would derive its timing (to obtain 100 Hz) from counting down the (approximately 50 kHz) frequency derived from the erection wand 30. Such switching circuits 78 are well known in the electronics art. Further, a rechargeable battery operated erection wand circuit that cause the 50 kHz current to flow in the coil 32 is also well known in the electronics art. Further, the design of circuitry to recharge the rechargeable battery of the wand 30 is also a well known art. Thus none of the details of the above mentioned circuits need to be described herein.

Figure 5:
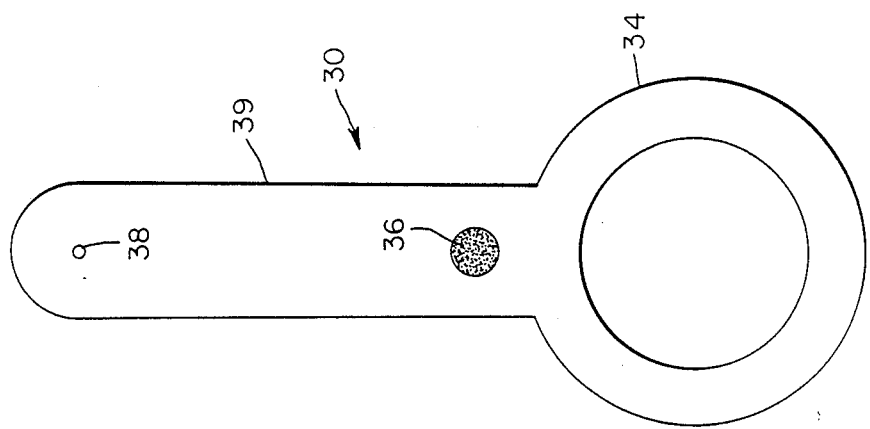
FIG. 5 is a plan view of the erection wand.

FIG. 5 is a plan view drawing of the erection wand 30 which shows a torrid 34 that surrounds the base of the penis, a push-for-on button 36 that must be pushed in order to activate the coil 32 that is contained within the torroid 34, and an indicator light 38 which flashes when the battery voltage is low. The battery which is in the handle 39 of the wand 30 can be recharged by means of an electrical receptacle in the handle 39 from a transformer and rectifier plugged into a regular house receptacle, or by magnetic induction. Both techniques are well known in the electronics art.

Figure 6:
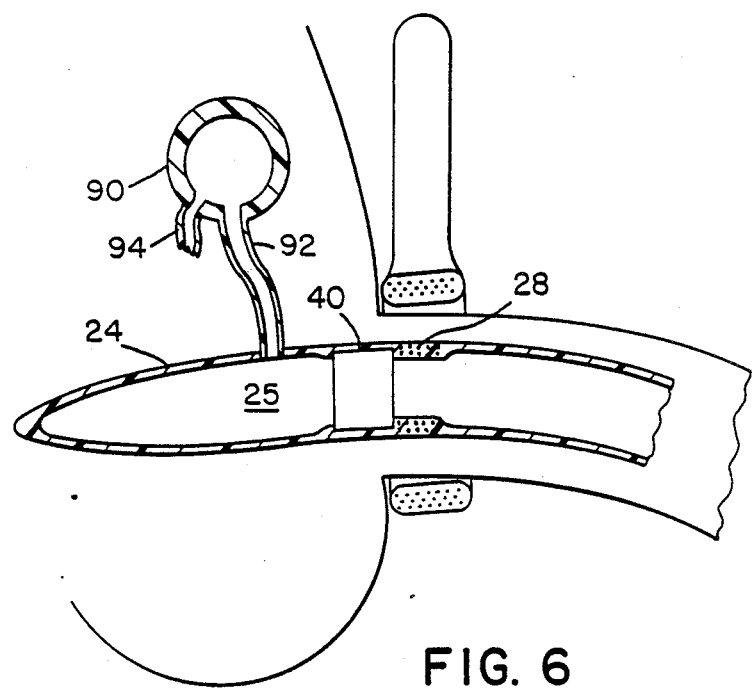
FIG. 6 is a cross-sectional view of a penile cylinder with a separate fluid reservoir.
Figure 7:
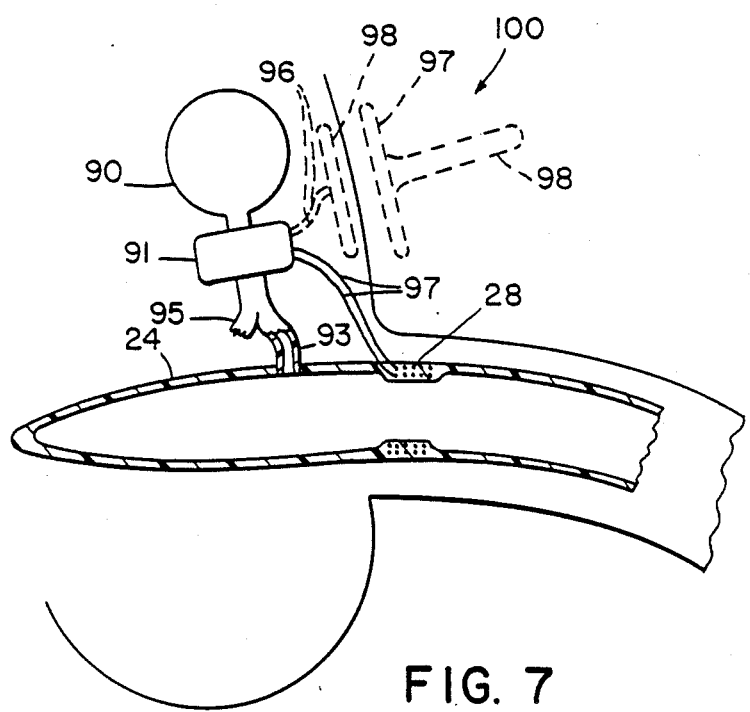
FIG. 7 is a cross-sectional view of a penile cylinder with a separate fluid reservoir and an induction coil implanted subcutaneously in the abdomen.

The invention described herein is optimum from the point of view of a minimum number of implanted parts. However, if more than approximately 5 ml is desired to be added to the pendulous chamber 23 to obtain a harder erect state, a separate fluid reservoir 90 located in the abdomen, as seen in FIG. 6, could be used which employs two output fluid lines 92 and 94 each connected to the root chambers 25 of two separate cylinders implanted in the penis. In FIG. 6, the separate cylinder to which the fluid line 94 is connected is not shown. The pumping means 40 could still be located and electrically powered as shown and described in FIGS. 1, 2, 3, 4 and 6, or, a single fluid pump 91 could be located in close proximity to the reservoir 90 as shown in FIG. 7. The induction coils 28 could be located as shown in FIG. 1 (or FIG. 7) and have wires 97 running to a single pump 91 at the reservoir 90 as one alternative embodiment of this invention as shown in FIG. 7. The single pump 91 would connect to two output fluid lines 93 and 95. The line 93 is shown connected to the root 24 of an implanted cylinder; the line 95 would be connected to a second cylinder (not shown) which would also be implanted in the penis. Alternatively, a single pick-up induction coil 98 could be implanted subcutaneously in the abdomen as shown by dotted lines in FIG. 7, with wires 96 connecting to the pump 91 which constitutes another alternative embodiment of this invention. An external power source 100, having an induction coil 97 connected to a handle 98 would provide the alternating magnetic field which is required to power the implanted induction coil 98 as shown by dotted lines in FIG. 7.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. An apparatus for achieving a penile erection in a human male, comprising:
    at least one elastomer cylinder having a root chamber and a pendulous chamber, said elastomer cylinder adapted to be placed in the corpus carvenosum of the penis;
    an external magnetic field generator which can be placed over some section of the penis which generates an alternating magnetic field;
    an induction coil contained within said elastomer cylinder which produces an alternating electric current when in the proximity of said alternating magnetic filed which is produced by said external magnetic field generator; and
    a fluid pumping means located within said elastomer cylinder, said pumping means being operated by the electrical power generated in said induction coil to pump fluid from said root chamber to said pendulous chamber in order to stiffen said elastomer cylinder for causing the erect state of the penis.

2. The apparatus of claim 1 wherein said pumping means is located between said root chamber and said pendulous chamber of said elastomer cylinder.

3. The apparatus of claim 1 wherein said pumping means is a pulsatile, solenoid pump that is operated at a frequency between 10 Hz and 1000 Hz.

4. The apparatus of claim 1 wherein said external magnetic field generator is in the form of a torroid attached to a handle, said handle being held by the user to place said torroid around that region of the penis where said induction coil is located within said elastomer cylinder.

5. The apparatus of claim 1 wherein said pumping means produces vibration that is perceived by the user to indicate that said external magnetic field generator is properly positioned.

6. The apparatus of claim 1 wherein said pumping means changes its vibration level when said root chamber is drained so as to indicate that the maximum hardness achievable for the erect state has been obtained.

7. The apparatus of claim 1 further comprising a check valve means connecting to said root chamber that opens at a set pressure thereby preventing over-pressurization of said pendulous chamber of said elastomer cylinder.

8. The apparatus of claim 7 wherein said check valve means can be opened at said set pressure by manually squeezing the penis in order to obtain the flaccid state by causing liquid to flow from said pendulous chamber to said root chamber.

9. The apparatus of claim 1 wherein said pumping means includes intake valve means and output valve means which cooperate to provide at least a 1.0 psi difference in the pressure between the greater pressure in said root chamber as compared to the lower pressure in said pendulous chamber when the flaccid state of the penis is achieved.

10. The apparatus of claim 9 wherein said intake valve means and said output valve means each employ a hard seat and a soft elastomer portion within their poppets.

11. The apparatus of claim 1 wherein the power source for said external magnetic field generator is rechargeable.

12. The apparatus of claim 1 wherein said induction coil is used to charge a capacitor whose discharge through the coil of an electromagnet causes said pumping means to operate.

13. The apparatus of claim 1 wherein a rigid member is placed longitudinally at the center of said root chamber to maintain the rigidity of said root chamber of the apparatus when said root chamber is collapsed to obtain the erect state.

14. An apparatus for achieving a penile erection in a human male comprising:
    at least one elastomer cylinder having a root chamber and a pendulous chamber, said elastomer cylinder adapted to be placed in the corpus carvenosum of the penis;
    an external magnetic field generator which can be placed over some section of the body to generate an alternating magnetic field;
    an induction coil contained within the body which produces an alternating electric current when in the proximity of said alternating magnetic field which is produced by said external magnetic field generator;
    a fluid reservoir implanted in the abdomen; and
    a fluid pumping means located within said apparatus, said pumping means being operated by the electrical power generated in said induction coil to pump fluid from said implanted fluid reservoir into said pendulous chamber of said elastomer cylinder in order to stiffen said elastomer cylinder for causing the erect state of the penis.

15. The apparatus of claim 14 wherein said induction coil is placed in the abdomen.

16. The apparatus of claim 14 wherein said induction coil is contained within said elastomer cylinder.

17. The apparatus of claim 14 wherein said pumping means is located between said root chamber and said pendulous chamber of said elastomer cylinder.

18. The apparatus of claim 14 wherein said pumping means is located adjacent to said fluid reservoir.

19. The apparatus of claim 14 wherein said pumping means is a pulsatile, solenoid pump that is operated at a frequency between 10 Hz and 1000 Hz.

20. The apparatus of claim 14 wherein said external magnetic field generator is in the form of a torroid attached to a handle, said handle being held by the user to place said torroid in close proximity to that region of the body where said induction coil is located.

21. The apparatus of claim 14 wherein said pumping means is capable of producing vibration that is perceived by the user to indicate that said external magnetic field generator is properly positioned.

22. The apparatus of claim 14 wherein said pumping means changes its vibration level when said root chamber is drained so as to indicate that the maximum hardness achievable for the erect state has been obtained.

23. The apparatus of claim 14 further comprising a check valve means connecting to said root chamber that opens at a set pressure thereby preventing over-pressurization of said pendulous chamber of said elastomer cylinder.

24. The apparatus of claim 23 wherein said check valve means can be opened at said set pressure by manually squeezing the penis in order to obtain the flaccid state by causing liquid to flow from said pendulous chamber to said root chamber.

25. The apparatus of claim 14 wherein said pumping means includes intake valve means and output valve means which cooperate to provide at least a 1.0 psi difference in the pressure between the greater pressure in said fluid reservoir as compared to the lower pressure in said pendulous chamber when the flaccid state of the penis is achieved.

26. The apparatus of claim 25 wherein said intake valve means and said output valve means each employ a hard seat and a soft elastomer portion within their poppets.

27. The apparatus of claim 14 wherein said external magnetic field generator uses a rechargeable battery.

28. The apparatus of claim 14 wherein said induction coil is used to charge a capacitor whose discharge through the coil of an electromagnet causes said pumping means to operate.

* * * * *